United States Patent [19]

Lai

[11] Patent Number: 5,081,164
[45] Date of Patent: Jan. 14, 1992

[54] ORGANOSILICON DENTAL COMPOSITE RESTORATIVE MATERIALS

[75] Inventor: Juey H. Lai, Burnsville, Minn.

[73] Assignee: Lai Laboratories, Inc., Apple Valley, Minn.

[21] Appl. No.: 626,622

[22] Filed: Dec. 7, 1990

Related U.S. Application Data

[63] Continuation-in-part of Ser. No. 510,100, Apr. 17, 1990, abandoned.

[51] Int. Cl.$^5$ .............. C08F 30/08; C08G 77/20; C08K 3/36; C08K 3/40
[52] U.S. Cl. ........................ 522/77; 522/908; 522/81; 522/99; 522/83; 523/116; 526/279
[58] Field of Search .............. 522/908, 99, 77; 523/116; 526/279

[56] References Cited

U.S. PATENT DOCUMENTS

| | | | |
|---|---|---|---|
| 3,066,112 | 11/1962 | Bowen | 523/116 |
| 3,709,866 | 1/1973 | Waller | 522/96 |
| 4,414,375 | 11/1983 | Neefe | 526/260 |
| 4,504,231 | 3/1985 | Koblitz et al. | 523/116 |
| 4,633,003 | 12/1986 | Falcetta et al. | 528/32 |
| 4,780,510 | 10/1988 | Uemiya et al. | 525/326.5 |

OTHER PUBLICATIONS

J. Dental Res. 6A, Abstract No. 30, 1985, "Evaluation of Siloxane-Containing Dental Composites", J. S. Kuo, J. M. Antonucci and W. Wu.

"Resin Based Dental Composites–An Overview", Joseph M. Antonucci, from Polymers in Medicine: Biomedical and Pharmaceutical Application, edited by E. Chiellini, P. Giusti, C. Migliaresi and L. Nicolai, Plenum Press, 1986.

Dialog Information Services, Inc., Prints Summary of patent search from 1971 to Mar. 1988.

*Primary Examiner*—Marion E. McCamish
*Assistant Examiner*—Susan Berman
*Attorney, Agent, or Firm*—Haugen and Nikolai

[57] ABSTRACT

A restorative dental composite material consists essentially of an organosilicon monomer selected from a class of siloxane materials which are cross-linkable utilizing visible light sensitive photoinitiators, an amount of filler material, a coupling agent and an amount of activator. An amount of ethylenically unsaturated monomer, an amount of thermally pre-polymerized particle material and/or a pigment material can be added to the composite if indicated. The materials exhibit greatly improved properties including a high degree of conversion, minimum water sorption and good color stability.

31 Claims, 1 Drawing Sheet

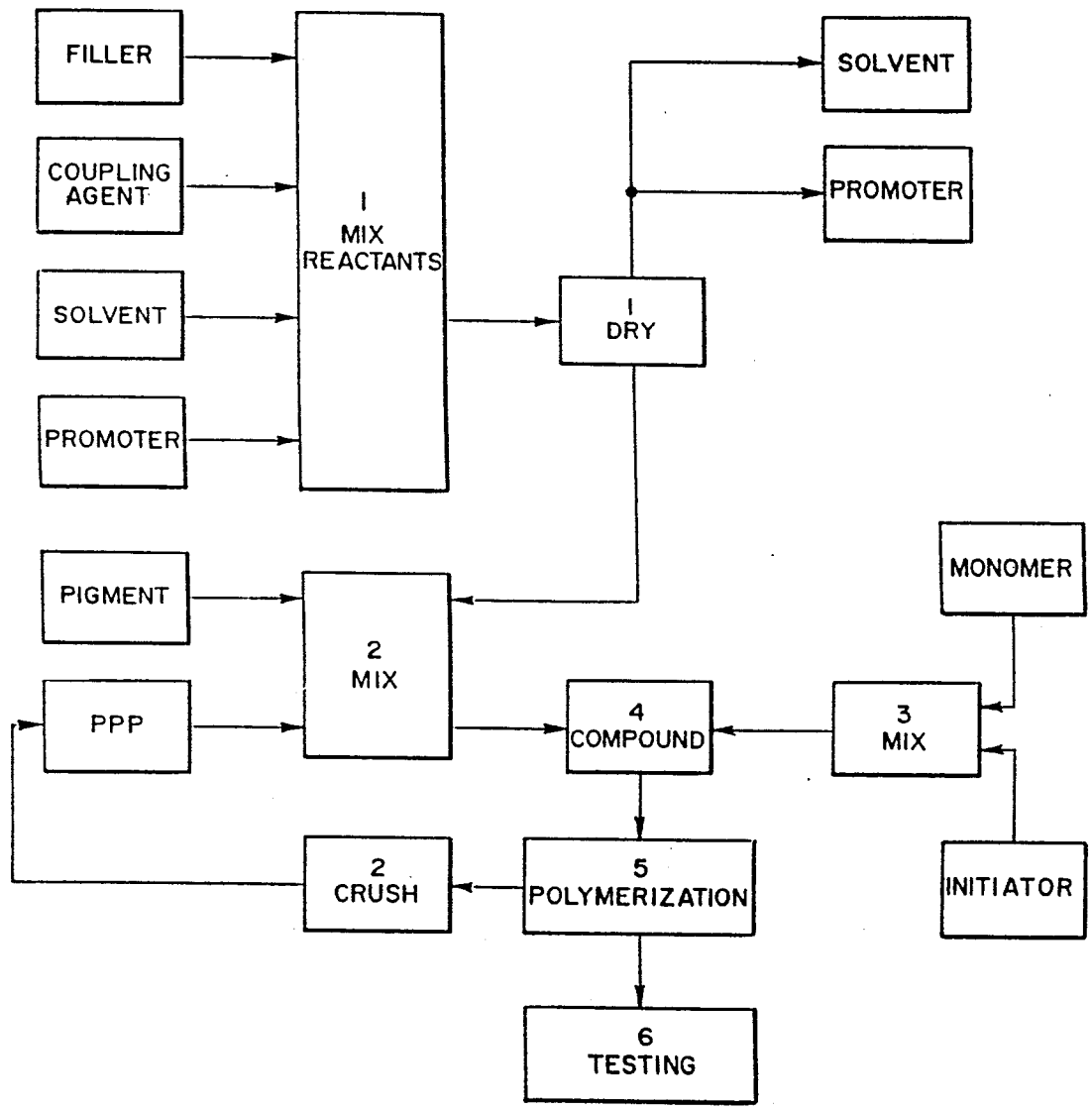

ORGANOSILICON DENTAL COMPOSITE RESTORATIVE MATERIALS

CROSS-REFERENCE TO RELATED APPLICATION

This application is a continuation-in-part of application Ser. No. 07/510,100, filed Apr. 17, 1990, now abandoned.

BACKGROUND OF THE INVENTION

I. Field of the Invention

The present invention relates to the field of restorative dentistry and, more particularly, to a class of visible light photocurable organosilicon composite materials suitable for both anterior and posterior tooth restoration.

II. Related Art

Composite dental restorative materials have been the subject of much research in recent years. Early work in the field includes that done by Bowen, exemplified by U.S. Pat. 3,066,112, which describes early composite dental restorative materials. Some of these materials have been gradually accepted as restorative materials for anterior teeth, however, when used as restorative materials for posterior teeth, the materials suffer from a number of shortcomings and, therefore, have not yet met with wide acceptance clinically.

Current composite dental restorative materials generally consist of a monomer, a ceramic filler, a photoinitiator, an activator, and a coupling agent. Upon exposure to light, the photoinitiator and the activator generate the free radicals which initiate the polymerization of the monomer. The polymer acts as the binder for the filler, and the coupling agent is used to bond the polymer and the filler. The monomers are generally high molecular weight dimethacrylates which are polymerizable by heat, chemicals, or light. A commonly used visible light initiator is camphorquinone which is used to initiate the polymerization in combination with an activator such as ethyl N,N-dimethyl aminobenzoate.

Major deficiencies of using composite materials as posterior restorative materials are lack of durability and color stability in the oral environment. Lack of durability is mainly due to loss of substance through wear, and loss of anatomic form due to microleakage caused by polymerization shrinkage and lack of adhesion of composites to tooth structure. Color instability of composite resins has been attributed primarily to oxidation of the residual photoinitiator, and the amine activator.

Significant research effort has been devoted to address the microleakage (marginal leakage) problem caused by polymerization shrinkage and lack of adhesion. Polymerization shrinkage can be minimized by using a high molecular weight monomer such as Bis-GMA, I, below, and by increasing the filler content in the composite. Bonding of dental composites to enamel can be improved by applying the acid-etch technique which creates microporosity on the surface of enamel by treating the surface with orthophosphoric acid. The technique provides mechanical interlocking of composites to the enamel surface. Although good adhesion between the composites and dentin is inherently more difficult, considerable progress has been made in recent years in developing coupling agents which can bond the dental composites to dentin surface. Commercial coupling agents based on phosphate derivatives of monomer dimethacrylate or an isocyanate derivative of an urethane dimethacrylate have been reported to have the property of producing good adhesion between the composite and dentin.

Wear mechanisms of dental composite materials in the oral environment appear to be complex. Wear is defined as unwanted removal of solid materials from the surface as a result of mechanical action and can include adhesive, abrasive, fatigue, corrosive, or chemical action. Many wear mechanisms have been proposed and postulated; but it is generally recognized that wear of polymer matrix through chemical and mechanical degradation, and loss of ceramic filler due to debonding between the filler and the polymer, are two important contributing factors. As the polymer matrix is removed from the surface of the restoration by abrasion and chemical degradation, more filler particles are exposed. Although filler particles are quite abrasion resistant, debonding between the polymer and the filler particle results in loss of filler particles thereby exposing more polymer surface. A high resistance to chemical degradation, and strong bonding between the polymer and the filler in the oral environment, are the two most important requirements for high performance dental composites.

Current polymer matrices used for dental restorative materials are based on free radical addition polymerization and cross-linking of high molecular weight monomers bisphenol A Bis(2-hydroxylpropyl) methacrylate, Bis-GMA, (I) or urethane dimethacrylates (II) (UDMA). Each monomer molecule of Bis-GMA and urethane dimethacrylate possesses two methacrylate groups (MA) (III), and each methacrylate group contains a carbon-carbon double bond where polymerization and cross-linking take place.

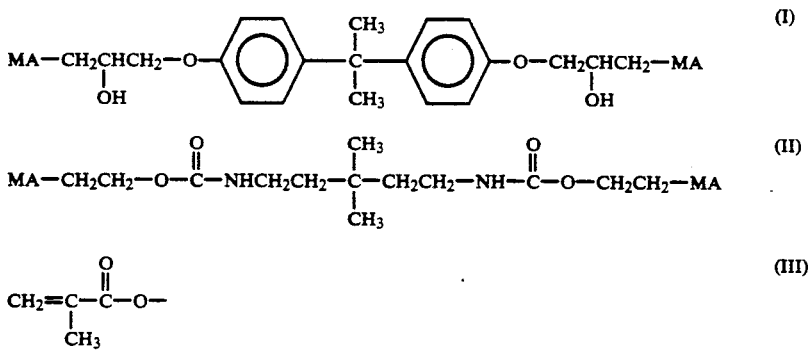

These high molecular weight monomers are highly viscous liquids, and diluents are often added to the composite for ease of handling and mixing. Diluents currently in use are generally dimethacrylate monomers of lesser viscosity, e.g. triethylene glycol dimethacrylate (TEGD) (IV).

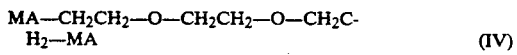

$$MA-CH_2CH_2-O-CH_2CH_2-O-CH_2CH_2-MA \quad (IV)$$

The viscous nature of the monomers and the rigid structure of the polymer backbones, however, also lead to a rather low degree of conversion associated with the polymerization of the monomer of approximately 50-70%. As the polymerization and cross-linking proceed, the diffusion rate of propagating free radicals, the unreacted monomer molecules, and the pendant methacrylate species are drastically reduced. The glass transition temperature increases with the degree of polymerization, and the segmental mobility of the polymer chains is also retarded. Consequently, the polymer matrix in the resulting composite materials retains a considerable number of unreacted methacrylate groups. The residual carbon-carbon double bonds in the unreacted methacrylate groups are susceptible to chemical degradation thus contributing to wear.

One polysiloxane material in the form of the amounts of the hydrophobic monomer Bis(3-methacryloxypropyl) tetramethyldisiloxane Bis-MPTMS (V)

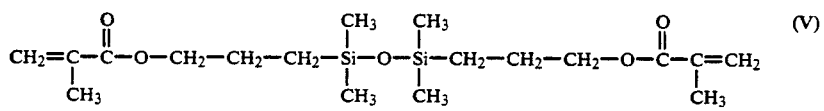

has also been used as a diluent for the base resins Bis-GMA (I), Bis-IGMA (a non-hydroxylated isomeric analog of Bis-GMA), and urethane dimethacrylate (UMDA) (II), in the formulation of certain dental composite restoratives. This was reported by J. S. Kuo, et al., in "Evaluation of Siloxane Containing Dental Composites", Journal of Dental Research Abstracts, 6A, Abstract No. 30 (1985).

The composites of Kuo are decidedly resin based materials which contain only a minor amount of the material Bis-MPTMS (V) which is added to reduce the high viscosity of the resin in the manner of the other diluents enumerated above. While some success may have been achieved cross-linking these materials and including fillers such as silanized radiopaque glass, the restorative materials of these combinations have been found to be generally lacking in the necessary hardness and mechanical properties demanded of permanent dental restorative materials. Also, polymers of the monomer Bis-MPTMS exhibit glass transition temperatures which are lower than desired.

Low degree of conversion has been recognized as a major polymerization shortcoming in prior dental composite resin technology. Low degree of conversion is intimately related to the flexibility of the polymer backbone. The high level of unreacted dimethacrylate groups associated with the low degree of conversion decreases the hardness, resistance to swelling, and increases the rate of wear. Thus, an alternate monomer which could yield high degree of conversion upon polymerization would be highly desirable as the polymer backbone matrix.

The mechanical properties of polymers can be significantly enhanced by the addition of reinforcing agents to form composite materials. In dental composite restorative materials, the addition of ceramic fillers has the effect of reducing polymerization shrinkage, decreasing thermal expansion, and increasing the hardness, strength and wear resistance of the materials. This superior performance, however, depends critically on the bonding between the polymer and the filler. Strong bonding between the polymer and the filler is needed for stress transfer across the interface thereby allowing the filler to share the stress thus providing the reinforcing effect.

The interaction between the polymer and the filler depends largely on the chemical structures of the polymer and the filler. In dental restorative materials, microcrystalline quartz, pyrogenic silicas, and radiopaque barium glasses have been frequently used as the fillers for the dimethacrylate polymers. The bonding between the polymers (derived from Bis-GMA and urethane dimethacrylates) and ceramic fillers, however, is inadequate without a coupling agent. Materials such as organosilanes have long been used as coupling agents in the dental composite materials to enhance the bonding.

Silane coupling agents currently used in bonding an inorganic substrate to a polymer have a general formula $R(CH_2)_nSi(OR')_3$, where R and R' are organoalkyl groups. The R groups usually contain carbon-carbon double bonds for bonding the polymer. The R'O groups are usually alkoxy or acetoxy groups which are hydrolyzable by water. The silane compound, γ-methacryloxypropyl trimethoxysilane (MPTS), $CH_2=C(CH_3)COO(CH_2)_3Si(OCH_3)_3$, is a coupling agent widely used in dental composites. The coupling agent MPTS comprises a methacrylate group through which the coupling agent is bonded to the methacrylate group of the monomer BIS-GMA (I) or urethane dimethacrylate (II). The coupling agent also contains three methoxy groups which, upon hydrolysis, generate silane triols. The silanol groups can undergo condensation reactions with silanol groups from the surface of the ceramic substrate such as silicon dioxide. The siloxane linkages formed by the condensation reactions provide the bonding between the coupling agent and the filler.

Debonding can occur either at the polymer-silane interface, or at the filler-silane interface, or both. However, it is generally agreed that debonding at the filler-silane interface due to hydrolysis of siloxane linkages in the oral environment is more probable. Hydrolytic stability of the siloxane bonds, therefore, is an important factor in determining material wear.

Hydrolytic stability of the siloxane bonds depends largely on the chemical nature of the filler and the silane coupling agent; however, it is known that the stability can be maintained by minimizing the exposure of the siloxane bonds to water. Thus, a hydrophobic polymer which can repel water, and thus minimize the hydrolysis of the siloxane bonds would be desirable as the polymer matrix.

Whereas silane compounds have found use as adhesives, and are suitable for use as coupling agents with respect to coupling ceramic filler materials to cross-linked siloxane materials, they themselves lack the properties necessary for successful use as primary restorative materials.

SUMMARY OF THE INVENTION

According to the present invention there has been discovered hydrophobic siloxane monomers with appropriate bonding groups in the monomer, which, due to the flexible nature of the siloxane bonds, yields a high degree of conversion upon polymerization which implies high cross-link density which not only enhances resistance to chemical degradation but also improves the mechanical properties, e.g. rigidity and hardness, of the polymer. Polymers based on the siloxane monomers exhibit minimum water sorption, due to their relatively high degree of hydrophobicity, minimum chemical degradation due to their high degree of conversion, and thereby enhance the wear resistance of the dental composites in the oral environment. The siloxane monomers are high molecular weight monomers that have aromatic groups in the chains to enhance the rigidity and mechanical strength of the polymer matrix. One class of siloxane monomers which possesses dimethacrylate or diacrylate groups at the ends can be represented by the chemical structure (VI) as shown next below:

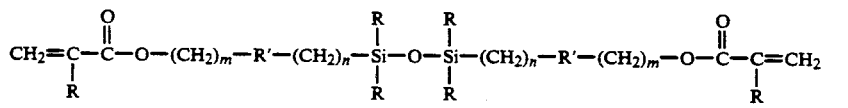

where R is either a hydrogen atom or an alkyl group having from 1 to 5 carbon atoms, R' is an aromatic group such as phenyl group, or substituted phenyl group, and n and m are integers usually equal to 1, and generally not greater than 2 to preserve a high degree of polysiloxane character in the polymers.

The siloxane monomers of the structure (VI) can be polymerized or cross-linked by thermal, chemical or photoinitiated means. They are miscible with the preferred photoinitiator and activators and the mixture are formulated to undergo polymerization and cross-linking upon exposure to visible light. The polymerization and cross-linking proceed by addition reactions without generating any gas or vapor. The preferred photoinitiator is camphorquinone. It is contemplated, however, that others having similar properties could be substituted. While the use of visible light for the curing of the composite is preferred for most applications, the use of ultraviolet light is also contemplated for others and no limitation to the visible light portion of the spectrum is intended. Activators include compounds such as Ethyl-4,N,N-dimethyl aminobenzoate, 2-dimethylamino ethyl methacrylate, and Dimethylamino phenethanol.

The photoinitiators and activators are generally polar compounds and the siloxane monomers possess a certain degree of polarity. This produces, in general, miscibility of these compounds in the preparations of the invention.

These are generally compounded in a formula including an amount of a ceramic-based filler material and a coupling agent to increase bonding of filler particles to the polymer matrix. The fibers may be any compatible ceramic and examples include various types of glass, silica and other materials. Coupling agents include organosilane compounds such as γ-methacryloxypropyl trimethoxysilane or vinyl triethoxysilane. In addition, an amount of finely divided pre-polymerized polysiloxane particles, normally polymerized using a thermal initiator such as benzoyl peroxide, can be added to the filler mix along with an amount of pigment. The composition of the pre-polymerized particles is preferably the same or similar to that of the siloxane of the composite material. The thermally cured pre-polymerized particles reduce the relative amount of photocuring required for the composite. The advantage of using the siloxane monomers characterized by structure VI are many. Since the monomers are more hydrophobic, they, in general, exhibit less water sorption. The presence of flexible siloxane bonds —Si—O—Si— in the monomers apparently increases the degree of conversion upon polymerization. Further, since siloxane monomers are generally less viscous than Bis-GMA, a diluent such as TEGDMA (triethyleneglycol dimethacrylate) required for Bis-GMA are not required for handling the siloxane monomers.

The siloxane monomers with structure VI are high molecular weight monomers and, therefore, generally should exhibit a low degree of polymerization shrinkage. The monomers contain dimethacrylate or diacrylate groups which are conducive to free radical polymerization and cross-linking by the visible light. The aromatic groups (R') in the middle of monomer chains should act to further enhance the rigidity and mechanical properties without hindering the polymerization and cross-linking of the dimethacrylate groups at the ends.

The hardness and mechanical properties of the siloxane monomer-based composites can be further enhanced by adding amounts of ethylenically unsaturated monomers such as diacrylates or dimethacrylates to the siloxane monomers. These combinations allow certain desirable properties of more than one monomer to be blended with others to achieve a desired result. The ingredients are compounded and, thereafter, can be stored in an environment that does not expose the composite materials to light, then utilized as needed in the dental environment to replace or mend natural dental materials by being polymerized in situ.

The first step in compounding the composite of the invention involves the treatment of the filler particles with a silane coupling agent. This requires the mixing of filler, coupling agent (CA), solvent and a promoter into a slurry. After the filler and CA react, the treated filler is dried by evaporation of the volatile solvent and promoter. A filler mixture is prepared by combining all the dry ingredients including the treated filler and coupling agents with a dry pigment or pigments, and, in certain cases, pre-polymerized particles (PPP) and mixing them together. Contemporaneously, the monomers for polymerization are mixed with the initiators and activator to prepare a monomer mixture. The filler mixture and the monomer mixture are then compounded together. This composite may be stored away from visible light until used. The compounded material is polymerized when desired in step five to form a light cured restorative composite in situ.

BRIEF DESCRIPTION OF THE DRAWINGS

The lone FIGURE is a schematic diagram of the process of making and testing restorative material in accordance with the invention.

DETAILED DESCRIPTION

The siloxane monomers in accordance with the invention are miscible with and polymerizable by a visible light photoinitiator and activator, are hydrophobic in nature, and upon polymerization have a high degree of conversion and sufficient mechanical strength for use as dental composite matrices. To minimize polymerization shrinkage, the siloxane monomers selected are high molecular weight monomers. The monomers are compounded with filler particles and polymerized (hardened) by the visible light. The performance of the composites had been evaluated in vitro according to ADA Specification #27. Although that specification appears to have been more particularly directed to chemically cured materials, it is the only one currently being used.

Specifically, the high molecular weight siloxane monomers selected have been mainly those which possess dimethacrylate or diacrylate groups at the ends illustrated by the structure VI. The advantages of using the siloxane monomers characterized by these structures are many. The monomers are more hydrophobic and exhibit less water sorption. The presence of flexible siloxane bonds —Si—O—Si— in the monomers appears to increase the degree of conversion upon polymerization. Further, since the siloxane monomers are generally less viscous than Bis-GMA, a diluent such as TEGDMA (triethyleneglycol dimethacrylate) required for Bis-GMA is not required for handling the siloxane monomers.

The siloxane monomers shown above are high molecular weight monomers and, therefore, should exhibit a low degree of polymerization shrinkage. The monomers contain either dimethacrylate or diacrylate groups which are conducive to free radical polymerization and cross-linking by the visible light. The aromatic groups (R') in the main chains are sufficiently far from the polymerizable groups which should enhance the rigidity and mechanical property of the polymers without hindering the polymerization and cross-linking of the dimethacrylate or diacrylate groups at the ends.

As shown in Examples 12-14, below, the curing can be made more efficient by including an amount of finely divided, thermally polymerized pre-polymerized material in the mix. The prepolymerized material may have the same composition as the material to be photopolymerized or of a different compatible composition. The pre-polymerized portion is cured using a thermal initiator such as benzoyl peroxide.

Certain of the materials which are exemplary and which have been found useful in compounding dental restorative materials in accordance with the invention are found in Tables I-IV which follow.

TABLE I
ORGANOSILICON MONOMER RESINS

MN-03: DPDD (1,3-divinyl-1,3-diphenyl-1,3-dimethyldisiloxane  (VII)

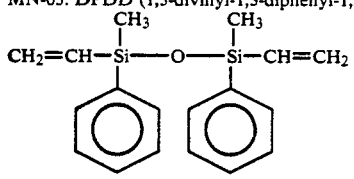

MN-05: DTMD (1,3-divinyltetramethyldisiloxane)  (VIII)

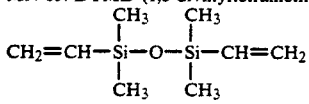

MN-06: DSPE [(p-dimethylsilyl)phenyl]ether  (IX)

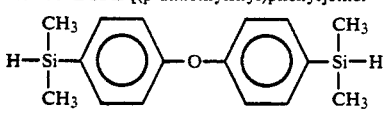

MN-07: 1,3-Bis [(p-acryloxymethyl)phenethyl]tetramethyl dixiloxane  (X)

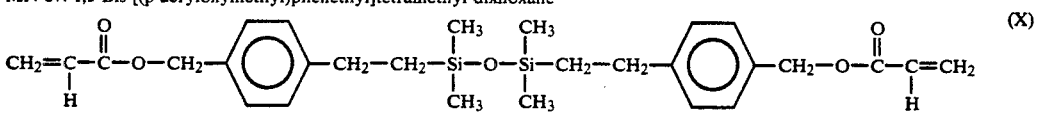

Bis-GMA: Bisphenol A bis(2-hydroxylpropyl)methacrylate  (XI)

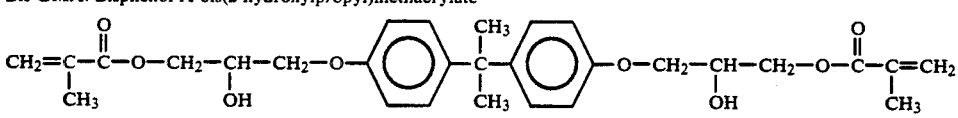

See also I.

TABLE II
PHOTOINITIATORS (PI), ACTIVATORS (AT), AND COUPLING AGENTS

Photoinitiators
Camphorquinone obtained from Aldrich Chemicals.

Activators

| Code  | Activator |
|-------|-----------|
| AT-01 | Ethyl-4,N,N-dimethyl aminobenzoate |
| AT-02 | 2-dimethylamino ethyl methacrylate |
| AT-03 | Dimethylamino phenethanol |

The activators were obtained from Aldrich Chemicals.

TABLE II-continued

PHOTOINITIATORS (PI), ACTIVATORS (AT), AND COUPLING AGENTS

Coupling Agents
(1) γ-methacryloxypropyl trimethoxysilane
(2) vinyl triethoxysilane
Both were obtained from Aldrich Chemicals.

TABLE III

FILLERS

| Code | Description (Vendor) | Particle size, μm | Refractive Index |
|---|---|---|---|
| F-01 | IMSIL A-108 (Ill. Minerals) microcryst. $SiO_2$ | 1.8 | 1.54–1.55 |
| F-02 | CAB-O-SIL-L-90 (Cabot Co.) amorphous fumed $SiO_2$ | 0.027 | 1.46 |
| F-03 | CAB-O-SIL-LM-130 (Cabot Co.) Amorphous fumed $SiO_2$ | 0.021 | 1.46 |
| F-04 | Siltex 44 (Kaopolite Inc.) amorphous fused $SiO_2$ | 8.8 | 1.46 |
| F-05 | Siltex 32 (Kaopolite Inc.) amorphous fused $SiO_2$ | 7.0 | 1.46 |
| F-06 | MIN-U-SIL 5 (US Silica) microcrys. $SiO_2$ | 1.1 | NA |
| F-07 | Siltex 22 (Kaopolite Inc.) amorphous fused $SiO_2$ | 5.0 | 1.46 |
| F-08 | MIN-U-SIL 10 (US Silica) microcry. $SiO_2$ | 1.7 | NA |
| F-09 | Aerosil OX 50 (Degussa Corp.) fumed $SiO_2$ | 0.04 | NA |
| F-10 | QUSO G35 (Degussa Corp.) precipitated $SiO_2$ | 3.0 average agglomerate size | NA |
| F-11 | Corning 7724 barium alumino borosilicate | 45 | 1.545 |

TABLE IV

PIGMENTS

| Pigment | Color | Vendor |
|---|---|---|
| $TiO_2$, rutile, 99.9% | white | Aldrich |
| $TiO_2$, rutile, 99.9% | white | Du Pont |
| Iron(111) oxide FeOOH ($Fe_2O_3$) | yellow | Mineral Pigment Co. |
| $Fe_3O_4$ | black | Mineral Pigment Co. |
| $Fe_2O_3$ | red | Mineral Pigment Co |
| $Fe_2O_3 + Fe_3O_4$ | brown | Mineral Pigment Co. |
| $Cr_2O_3$ | green | Mineral Pigment Co. |

Specific examples of monomers are discussed below. Several materials of the invention were made in accordance with procedures outlined in the several examples below. The equipment of the examples included that which will next be described.

Equipment

A visible light cure unit was used to initiate the polymerization in the composite. The particular unit used was a Visilux 2 from 3M Company of St. Paul, Minn. Other visible light curing units such as one available from Healthco can also be used. The Visilux 2 has a standard 8 mm diameter lightguide tip and an optional 13 mm diameter tip. The smaller tip was used for exposing composites in the 6 mm diameter molds, and the larger tip for 20 mm molds. According to the manufacturer, the maximum intensity is at 468 nm (blue region) which also coincides with the absorption maximum for the initiator, camphorquinone.

Darkroom safelights were used to prevent premature exposure of the visible light sensitive composites during preparation. The safelights provide red and infrared radiation, while the composites are reactive toward blue and ultraviolet. Two types of safelights were used. The first one was a Paterson Darkroom Safelight. The second type was a system made by using a Kodak GBX-2 filter in conjunction with a 15w bulb. The GBX-2 filter was designed specifically for blue and green sensitive dental and medical x-rays. No sample hardened prematurely while using these lights.

Stainless steel molds were used as they are required in all tests by the standards of American Dental Associates (ADA) Specification #27 (for direct filling materials) except the working time test. The following three types were used:

| ID (mm) | Height (mm) |
|---|---|
| 6 (+/−0.1) | 3(+/0.1) |
| 20 (+/−0.1) | 1(+/−0.05) |
| 20 (+/−0.1) | 7(+/−0.1) |

All interior surfaces have a 16 micro finish, which is the smoothest finish available with machined stainless steel. The 6 mm × 3 mm mold was used for the hardness and diametral tensile strength tests, the 20 mm × 1 mm mold for the opacity, color stability and water sorption tests, and the 20 mm × 7 mm mold for the hardening time test.

A Barcol Hardness tester model GYZJ934-1 manufactured by Barber Coleman of Rockford, Ill. was used to determine the hardness of the cured composite materials. It also is required to meet the ADA Specification #27 hardening time test. The tester was calibrated using two standard test discs and adjusting the output until the readings fell into the acceptable range for each disc.

Other equipment included a magnetic stirrer (Corning) for mixing monomers and photoinitiators, an analytical balance (Shimadzu) for all weighing, an oven (Tempcon) and an incubator (Boekel) for controlled temperature environments, and a Blak-ray J-221 Long Wave UV meter (UVP Inc.) for the color stability test.

Process Sequence

The process sequence for the production of dental composites includes five steps. A sixth step illustrated in the FIGURE involves testing the composites for various qualities. These steps will next be generally described.

The first step involves the treatment of the filler particles with a silane coupling agent. This requires the mixing of filler, coupling agent (CA), solvent and a promoter into a slurry. After the filler and CA react, the treated filler is dried by evaporation of the volatile solvent and promoter.

The second step involves the preparation of the filler mixture in which all the dry ingredients including the filler and coupling agents from step one are combined with a dry pigment or pigments, and, in certain cases, pre-polymerized particles (PPP), and these are thoroughly mixed together. In step three, which generally occurs contemporaneously with steps one and two, the monomers for polymerization are mixed with the initiators and activators to prepare a monomer mixture. In step four the filler mixture and the monomer mixture are compounded together. The compounded material is polymerized in step five to form either a light cured or thermally cured, in the case of PPP composite. This step would occur in situ in the case of actual dental restoration. The hardened composite is tested in terms of hardness, diametrical tensile strength and water sorption as in step six.

With respect to the examples, further process details will be presented. The treatment of the fillers was accomplished by creating a slurry of the silica filler in a solution of the coupling agent. The desired amount of filler was weighted out into a 250 ml beaker. Cyclohexane was added, usually in the ratio 2 ml/g filler for 1-10 $\mu$m particles or 15 ml/g filler for 0.01-0.04 $\mu$m particles. This slurry was then stirred on a magnetic stirrer for one half hour. The slurry was removed from the stirrer and $\gamma$-methacryloxypropyl trimethoxysilane coupling agent (CA) was added based on doubling the following amounts (since these calculated amounts represent the minimum required to coat the surface):

| m2/g Filler | Avg. Diam. | gCA/g Filler |
|---|---|---|
| 5.2 | 4.5 $\mu$m | 0.0257 |
| 6.3 | 1.8 $\mu$m | 0.0311 |
| 100 | 0.027 $\mu$m | 0.494 |

The promoter, n-propyl amine (NPA), was added in the quantity 0.4 times the weight of CA added. The slurry was then mixed on the magnetic stirrer for one hour allowing the CA to react with the filler silanol groups. The slurry was then dried in a hood.

Once the filler was dried, it was placed in the oven at 40 (+/−5) ° C. for one hour. The temperature was then elevated to 110 (+/−5) ° C. for two hours. The filler was allowed to cool in the room and then broken up and crushed in the beaker. After it was ground sufficiently (i.e. elimination of visible chunks), the treated filler was stored at room temperature.

The dry ingredients were weighed and mixed together. These included the treated filler, and, where used, pigments and pre-polymerized particles (PPP). Each component was weighed and these powders were then mixed and ground together with a Teflon TM coated spatula in a weigh boat until the powder appeared homogeneous. The combined powder was stored in glass vials at room temperature.

All monomers and polymerization initiators were combined in a mixture. The components were weighed into a 125 ml glass beaker. The monomers were weighed first and then initiators. Monomers that were very viscous (e.g. Bis-GMA) were placed in the beaker with a polypropylene stirring rod. Less viscous monomers were added using pipets or eye droppers.

Once all the components were added, the mixture was covered with a parafilm and placed on a magnetic stirrer. The time required to obtain a homogeneous mixture varied from 30 min to 4 hours, depending on the components, their solubilities and viscosities. The final mixture was transferred by eye dropper to a glass vial covered with aluminum foil and placed in the refrigerator (0° C.).

To form a composite the filler and monomer mixtures were added together and mixed. First, the monomer mixture was warmed to room temperature and weighed into a 125 ml glass beaker. This composite was mixed together with a polypropylene stirring rod by scraping all the liquid together. The mixing continued until all the filler was absorbed into the composite. All the material was incorporated in order to control the final composition. The final composite was placed in a glass vial, wrapped in aluminum foil to prevent exposure to any light and stored in a refrigerator (0° C.).

The light cured composites were all exposed using the Visilux 2 light curing unit. Under darkroom conditions, the material was placed into a mold sandwiched between two clear glass microscope slides (1 mm thickness). The surfaces in contact with the composite were usually coated with a thin layer of Dow Corning high vacuum grease to facilitate the release of the cured sample. After filling the mold to a slight excess, the other slide was pressed onto the top of the mold. This sandwich was then placed on a micro lab jack and raised up to the tip of the light curing unit. Once the tip was flush to the slide, the light was turned on.

A mold of 3 mm height and 6 mm inner diameter was used for the Barcol Hardness test and the diametrical tensile strength test. The 8 mm diameter light guide was always used with the 6 mm ID mold. The top and bottom were exposed one minute on each side for the diametrical tensile strength test, while only the top side was exposed for the hardness test. Some deviations from this procedure were attempted. For example, a 1 mm height and 20 mm ID mold was used initially along with repeated exposures in order to cover the entire surface area. However, the above conditions became standard and hardness values reported are for these conditions unless otherwise noted.

For the water sorption test the 1 mm x 20 mm mold was used (as required by the ADA Specification #27). In this test the 13 mm diameter light guide was used with seven one minute exposures only on the top side. The exposures were at various points in order to expose the entire sample.

Some of the composites were compounded using an amount of pre-polymerized particles in the mix, usually using the same monomer as the general composite. Thermal curing was used for pre-polymerized particle formulations PPP and benzoyl peroxide was the preferred thermal initiator. In this operation, benzoyl peroxide (1.0%) was first dissolved in the siloxane monomer, and the solution was mixed with predetermined amount of ceramic filler. The monomer and filler mixture was then thoroughly mixed, and placed in a stainless steel mold sandwiched between glass slides to prevent oxygen inhibition of the free radical polymerization and cross-linking. The samples were then placed in the oven for curing and hardening, at 70° C. for 3 hours and thereafter at 100° C. for 4 hours. After cooling to room temperature, the cured composites were crushed into small fragments and then the fragments were ground to a powder with a mortar and pestle or using an electric grinder. The powder was stored at room temperature in glass vials.

A Barcol model GYZJ934-1 was used to evaluate the hardness of composites. Initially these tests were performed on samples with a height of 1 mm and diameter of 20 mm. These samples broke frequently upon application of the tester and were more complex to photocure (several points required exposure). Consequently, 3 mm×6 mm molds were used and the samples tested while still in the mold (glass slides removed). Generally eight readings were taken on the top and eight on the bottom. The indenter was moved around the surface to prevent testing on the same spot. If the hardness value was unusually low, then that reading was discarded. In some cases the sample would fracture upon application of the tester. In this case, only readings obtained before the fracture were considered valid. Standard deviation ranged from 2-10%. The reported hardness values are for the top side only.

The average of the readings was corrected based on the hardness reading of a standard disc. The standard disc has a hardness of 87-89 or an average of 88. If the tester read an 86 on the standard, then the tester was reading too low and the average obtained for the composite was corrected upward.

A Comten Model 922MTT-20/02 Tensile Tester was employed to determine the diametral tensile strength of the composites in accordance with ADA Specification #27. The composite specimen were prepared by the procedure described previously using 6 mm×3 mm molds covered by glass plates After exposure, the assembly (the specimen in the molds covered by glass plates) was placed in an incubator wherein the temperature was maintained at 37±1° C. and the relative humidity at 95±5% for 15 minutes. The specimen disk and the mold were removed and the ends ground flat with 240 grit silicon carbide and water. The specimen was then ejected from the mold and stored in distilled water at 37±1° C. for 24 hours.

The specimen was then placed on its side between parallel platens of the tester for the tensile test. A small piece of blotting paper wet with water was inserted between the platen of the tester and each side of the specimen. The specimen was loaded continuously in compression at 1 cm/min to the breaking point. The diametral tensile strength was computed as follows:

$$T_s = 2P/\pi dl,$$

where
$T_s$ = tensile strength in MN/m$^2$,
P = load at fracture in N,
d = diameter of specimen in mm, and
l = length of specimen in mm.

Testing for water sorption was in accordance with ADA Specification #27. Three samples of each formulation were made. These samples were dried until the weight loss was less than 0.5 mgm/day. That weight was recorded and the samples submerged in distilled water maintained at 37° C. After one week the samples were weighted again and the difference of the weights was divided by the surface area of the sample to obtain the water sorption value in mgm/cm$^2$. The three samples were then averaged to obtain the value for the formulation.

The following specific examples illustrate certain embodiments in accordance with the invention. They are by no means meant to be in any manner limiting as to the scope of the invention.

EXAMPLE 1

1.4458 gm of X (TABLE I), 1,3-Bis(p-acryloxymethyl) phenethyl]tetramethyldisiloxane, was placed in a 25 ml glass vial, into which 18.7 mgm of benzoyl peroxide was added. The mixture was stirred for an hour until all the benzoyl peroxide was dissolved. The 0.7573 gm of inorganic filler, Aerosil OX50 (Degussa Corp.) which is a fumed SiO$_2$ and which has been treated with organosilane coupling agent γ-methacryloxypropyl trimethoxysilane was added to the mixture and mixed thoroughly. The homogeneous composite mixture was then placed in 20 mm×6 mm circular stainless steel mold with both sides covered by glass plates. The composites filled up the entire mold to eliminate the air inside the mold. The monomer and the filler mixture was then cured (polymerization and cross-linking) for one hour at 60° C., one and one half hour at 70° C. and two and one half hours at 100° C. The cured polymer composite was white and translucent. The hardness determined by using the Barcol Hardness instrument was 33.

EXAMPLE 2

1.4401 gm of 1,3-Bis[(p-acryloxymethyl) phenethyl]-tetramethyldisiloxane was placed in a 25 ml glass vial. A 17.5 mgm of photoinitiator camphorquinone and 17.7 mgm of activator ethyl-4,N,N-dimethyl aminobenzoate were then successively added to the monomer. The mixture was then stirred until the photoinitiator and the activator completely dissolved. The addition and the mixing were performed in a dark room with the aid of a Kodak GBX-2 darkroom safelight to prevent the photo-induced polymerization. After thorough mixing, the homogeneous mixture was contained inside a 3 mm×6 mm stainless steel mold which was covered with glass plates on both sides. The monomer mixture was then exposed with a visible light source, e.g. Visilux 2 (3M Co.) for 3 minutes, on both sides. The monomer polymerized and cross-linked immediately upon exposure to the visible light. The photocured polymer was transparent, brittle and showed a light yellowish color.

EXAMPLE 3

1.3612 gm of 1,3-Bis[(p-acryloxymethyl) phenethyl]-tetramethyldisiloxane was placed in a 25ml glass vial. 15.3 mgm of photoinitiator comphorquinone and 13.6 mgm of activator ethyl-4,N,N-dimethyl aminobenzoate were successively added to the monomer. The mixture was then stirred as in Example 2. After thorough mixing, 1.0120 gm of inorganic filler, Aerosil OX50 (Degussa Corp.) which is a fumed SiO$_2$ and which had been treated with the organosilane coupling agent γ-methacryloxypropyl trimethoxysilane was added to the monomer mixture. The filler also contained a small amount of TiO$_2$ pigment. The composite was thoroughly mixed until a homogeneous mixture was obtained. A small amount of the monomer/filler composite mixture was placed inside a 6 mm×3 mm stainless steel mold until it filled up the mold, and both sides of the mold were covered with glass plates. The monomer/filler composite was exposed by a visible light source, e.g. Visilux 2 (3M Co.) for three minutes on one side. The cured polymer composite was milky white and translucent, and exhibited natural tooth color. The hardness determined by Barcol Hardness instrument was 38.

EXAMPLE 4

The monomer/filler mixture prepared according to Example 3 was polymerized and tested to determine water sorption of the material according to New American Dental Association Specification #27 for Direct Filling Resins. 0.5027 gm of the composite was placed inside a 20 mm×1 mm stainless steel mold and cured with the Visilux 2 light cure unit. The exposure was one minute each at seven points across the resin disk. The cured sample disk was then placed inside a desiccator and dried at 37° C. until constant weight was obtained. The cured composite disks were then immersed in distilled water at 37° C. for a week. The weight gain of the disk was determined after surface moisture was blotted away. Water sorption expressed in milligrams per cm$^2$ was obtained by dividing the weight gain by the surface area of the disk.

The water sorption of the restorative material was determined to be only 0.16 mgm/cm$^2$. This is significant because it represents the lowest gain measured among known dental composites. The composite restorative material also exhibited good color stability after immersion in water at 37° C. for a week.

EXAMPLE 5

1.8612 gm of 1,3-Bis[(p-acryloxymethyl) phenethyl]-tetramethyldisiloxane was placed in a 25ml glass vial. 19.8 mgm of photoinitiator camphorquinone and 18.2 mgm of activator ethyl-4,N,N-dimethyl aminobenzoate were successively added to the monomer. The mixture was then stirred as in Example 2. After thorough mixing, 1.2456 gm of inorganic filler, Aerosil OX50 (Degussa Corp.) which had been treated with the organosilane coupling agent vinyl triethoxysilane (a different coupling agent from Example 3) was added to the monomer mixture. The monomer/filler composite mixture was thoroughly mixed until a homogeneous mixture was obtained. A small amount of the monomer/filler composite mixture was placed inside 20 mm×1 mm stainless steel mold until it filled up the mold, and both sides of the mold were covered with glass plates. The monomer/filler composite was exposed by a visible light source, e.g. Visilux 2 (3M Co.) for one minute each at seven points across the resin disk. The cured polymer composite was milky white and translucent, and exhibited natural tooth color. The hardness determined by the Barcol Hardness instrument was 45.

EXAMPLE 6

The monomer/filler mixture prepared according to Example 5 was polymerized and used to determine the water sorption of the dental composite restorative material according to new American Dental Association Specification #27 for Direct Filling Resins. The cured polymer composite disks were prepared according to the procedure described in the Example 4. A 0.4543 gm of the resin was placed inside a 20 mm×1 mm stainless steel mold and cured with the Visilux 2 light cure unit. The exposure was one minute each at seven points across the disk. The cured sample disk was then placed inside a desiccator and dried at 37° C. until constant weight is obtained. The cured composite disk is then immersed in distilled water at 37° C. for a week. The weight gain of the disk was determined as in Example 4.

The water sorption of the restorative material was determined to be 0.16 mgm/cm$^2$ equalling the significant low figure of Example 4. This material also exhibited excellent color stability after immersion in water at 37° C. for a week.

EXAMPLE 7

1.8134 gm of 1,3-Bis[(p-acryloxymethyl) phenethyl]-tetramethyldisiloxane was placed in a 25 ml glass vial. 19.0 mgm of photoinitiator camphorquinone and 136.9 mgm of activator 2-dimethylamino ethylmethacrylate were successively added to the monomer. The mixture was then stirred as in Example 2. After thorough mixing, 1.0367 gm of inorganic filler, Aerosil OX50 (Degussa Corp.) which had been treated with the organosilane coupling agent γ-methacryloxypropyl trimethoxysilane, as in Example 3, was added to the monomer mixture. The monomer/filler composite was exposed by a visible light source, e.g. Visilux 2 (3M Co.) for three minutes on one side. The cured polymer composite was milky white and translucent, and exhibited a color which closely resembled natural tooth color. The hardness of the cured composite resin determined by Barcol Hardness instrument was 30. Water sorption of the cured polymer composite determined by the procedure described in Example 4 was 0.35 mgm/cm$^2$, which was somewhat higher than the material of Examples 4 and 6 but still lower than the currently known commercial dental composites. Color stability remained good through the water sorption test.

EXAMPLE 8

1.2680 gm of 1,3=Bis[(p-acryloxymethyl) phenethyl]tetramethyldisiloxane was placed in a 25 ml glass vial, into which 0.8019 gm of Bis-GMA, bisphenol A bis(2-hydroxylpropyl) methacrylate was added as a comonomer. A 17.5 mgm of photoinitiator camphorquinone and 17.7 mgm of activator dimethylamino phenethanol were then successively added to the monomer mixture. The mixture was then stirred as in Example 2. After thorough mixing, the homogeneous mixture was contained inside a 3 mm×6 mm stainless steel mold which was covered with glass plates on both sides. The monomer mixture was then exposed with a visible light source, e.g. Visilux 2 (3M Co.) for three minutes on one side. The monomer mixture polymerized and crosslinked immediately upon exposure to the visible light. The photocured copolymer was transparent, brittle and showed light yellowish color.

EXAMPLE 9

0.9973 gm of 1,3-Bis[(p-acryloxymethyl) phenethyl]-tetramethyldisiloxane was placed in a 25 ml glass vial, into which 0.6306 gm of Bis-GMA, bisphenol A bis(2-hydroxylpropyl) methacrylate was added. A 15.4 mgm of photoinitiator camphorquinone and 15.8 mgm of activator dimethylamino phenethanol were then successively added to the monomer mixture. The mixture was then stirred as in Example 2. After thorough mixing, 0.8918 gm of inorganic filler, Aerosil OX50 (Degussa Corp.) which had been treated with the organosilane coupling agent γ-methacryloxypropyl trimethoxysilane was added to the monomer mixture. The monomer/filler composite mixture was thoroughly mixed until a homogeneous mixture was obtained. The addition and the mixing were performed in a darkroom under darkroom safelights. A small amount of the monomer/filler composite mixture was placed inside a 6 mm×3 mm stainless steel mold until it filled the mold; both sides of the mold were covered with glass plates. The monomer/filler composite was exposed by a visible light source, e.g. Visilux 2 (3M Co.) for 1.5 minutes on each side.

The resulting photocured copolymer composite was milky white and translucent, and exhibited a color closely resembling natural tooth color. The hardness of the photocured copolymer composite as determined by Barcol Hardness instrument was 51.

EXAMPLE 10

0.2012gm of 1,3-Bis(3-methacryloxypropyl) tetramethyldisiloxane was placed in a 25ml glass vial, into which 0.2012 gm of Bis-GMA, bisphenol A bis(2-hydroxylpropyl) methacrylate, was added. A 6.2 mgm of photoinitiator camphorquinone and 6.2 mgm of activator dimethylamino phenethanol were then successively added to the monomer mixture. The mixture was then stirred as in Example 2. After thorough mixing, 0.8984 gm of inorganic filler, Aerosil OX50 (Degussa Corp.), treated as in Example 9, was added and the composite was molded and cured as in Example 9 except that each side was exposed for 1.0 minute instead of 1.5 minutes. The photocure copolymer composite had a faint yellowish and amber color, and was translucent. The hardness of the cured copolymer composite as determined by Barcol Hardness instrument was 60.

EXAMPLE 11

0.1213 gm of 1,3-Bis(3-methacryloxypropyl) tetramethyldisiloxane was placed in a 25ml glass vial, into which 0.1819 gm of Bis-GMA, bisphenol A bis(2-hydroxylpropyl) methacrylate, was added. A 4.5 mgm of photoinitiator camphorquinone and 4.5 mgm of activator dimethylamino phenethanol were then successively added to the monomer mixture. The mixture was then stirred as in Example 2 and, after thorough mixing, 0.7071 gm of inorganic filler, Aerosil OX50 (Degussa Corp.) treated as in Example 9 was added and the molding and polymerization carried out as in Example 9 except that exposure was for one minute on each side. The photocured copolymer composite has faint yellowish and amber color, and is translucent. The hardness of the cured copolymer composite as determined by Barcol Hardness instrument is 65.

EXAMPLE 12

0.34521 gm of 1,3-Bis(3-methacryloxypropyl) tetramethyldisiloxane, was placed in a 25 ml glass vial, into which 0.5177 gm of Bis-GMA, bisphenol A bis (2-hydroxylpropyl) methacrylate, was added. Then 12.9 mgm of benzoyl peroxide was added and stirred for an hour until all benzoyl peroxide was dissolved in the comonomer mixture. 2.1753 gm of inorganic filler, Aerosil OX50 (Degussa Corp.) which had been treated with organosilane coupling agent $\gamma$-methacryloxypropyl trimethoxysilane was added to the mixture and mixed thoroughly. The homogeneous composite mixture was then placed in a 20 mm $\times$ 6 mm circular stainless steel mold with both sides covered by glass plates. The composite was used to fill the entire mold to eliminate the air inside the mold. The monomer and the filler mixture was then cured (polymerization and cross-linking) for three hours at 70° C., and four hours at 100° C. The cured polymer composite was hard, white and translucent.

EXAMPLE 13

0.1387 gm of 1,3-Bis(3-methacryloxypropyl) tetramethyldisiloxane was placed in a 25ml glass vial, into which 0.2230 gm of Bis-GMA, bisphenol A bis(2-hydroxylpropyl) methacrylate, was added. A 9.3 mgm of photoinitiator camphorquinone and 9.3 mgm of activator dimethylamino phenethanol were then successively added to the monomer mixture. The mixture was then stirred until the photoinitiator and the activator were all dissolved. After thorough mixing, 0.5948 gm of inorganic filler, Aerosil OX50 (Degussa Corp.) which is a fumed $SiO_2$ and which had been treated with $\gamma$-methacryloxypropyl trimethoxysilane was added to the monomer mixture. An amount of the copolymer 1,3-Bis(3-methacryloxypropyl) tetramethyldisiloxane and bisphenol A bis(2-hydroxylpropyl) methacrylate prepared according to the procedure described in Example 12 was ground into fine powders and 0.6809 gm of the copolymer powder was added as pre-polymerized powder (PPP) to the monomer/filler composite mixture. The entire mixture was thoroughly mixed until a homogeneous mixture was obtained. The addition and the mixing were again performed in a darkroom with safelights to prevent photo-induced polymerization. A small amount of the monomer/filler composite mixture was placed inside 6 mm $\times$ 3 mm stainless steel mold until it filled up the mold, and both sides of the mold were covered with glass plates. The monomer/filler composite was exposed by a visible light source, e.g. Visilux 2 (3M Co.) for one minute on each side. The photocured copolymer composite was translucent and had amber color, and approached natural tooth color. The hardness of the cured copolymer composite as determined by Barcol Hardness instrument was 65.

EXAMPLE 14

The organosiloxane dental composite based on monomer mixture of 1,3-Bis(3-methacryloxypropyl) tetramethyldisiloxane and bisphenol A bis(2-hydroxylpropyl) methacrylate was prepared according to the formulation and procedure described in the Example 13 with on exception. The inorganic filler was premixed with 0.09% of $TiO_2$ before adding it to the monomer mixture and the copolymer composite powders. The entire mixture was thoroughly mixed until a homogeneous mixture was obtained. A small amount of the monomer/filler/powder composite mixture was placed inside the mold and was exposed by a visible light source, e.g. Visilux 2 (3M Co.) for one minute on each side. The photocured copolymer composite was translucent and milky white, and exhibited a natural tooth color. The hardness of the cured copolymer composite as determined by Barcol Hardness instrument was 66.

EXAMPLE 15

0.9931 gm of 1,3-Bis[(p-acryloxymethyl) phenethyl]-tetramethyldisiloxane was placed in a 50ml glass vial. 10.1 mgm of photoinitiator camphorquinone and 4.6 mgm of activator 2-dimethylamino ethyl methacrylate were successively added to the monomer. The mixture was stirred for an hour until the photoinitiator and the activator were all dissolved. The addition and the mixing were performed in a dark room with the aid of a Kodak GBK-2 darkroom safelight to prevent the photo-induced polymerization. An inorganic filler mixture was first prepared and added to the monomer mixture. The filler mixture consisted of 0.2781 gm of fumed silica ($SiO_2$) Aerosil OX50 (Degussa Corp.) and 4.1875 gm of microcrystalline silica IMSIL A-108 (Illinois Minerals). Both fillers had been treated with organosilane coupling agent $\gamma$-methacryloxypropyltrimethoxysilane before mixing. The monomer/filler composite mixture was thoroughly mixed until a homogeneous mixture was obtained. A small amount of the monomer/filler composite mixture was placed inside of a 6 mm $\times$ 3 mm stainless steel mold until it filled the mold; both sides of the mold were covered with glass plates. The monomer/filler composite was exposed by using a visible light source, e.g. Visilux 2 (3M Co.) for 1 minute on top side. The cured polymer composite was milky white and translucent. The hardness determined by Barcol Hardness instrument was 78. The water sorption of the composite restorative material determined according to the procedure described in the Example 4 was 0.23 mgm/cm.

EXAMPLE 16

The siloxane monomer/filler mixture prepared according to Example 5 was used to determined the diametral tensile strength of the organosilicon dental composite restorative material according to New American Dental Association Specification No. 27 for Direct Filling Resins. A Comten Model 922MTT-20/02 Tensile Tester was employed to determine the tensile strength. The cured polymer composite disks were prepared by the method similar to the procedure described in the Example 5 for hardness measurement except that the sample disks were exposed 1 minute on both sides. After exposure, the assembly was placed in a incubator with temperature maintained at 37±1° C. and relative humidity at 95±5% for 15 minutes. The specimen disk and the mold were removed and the ends ground flat with 240 grit silicon carbide and water. The specimen was then ejected from the mold and stored in distilled water at 37±1° C. for 24 hours. The specimen was then placed on its side between parallel platens of the tester and was loaded continuously in compression at 1 cm/min to the breaking point. The diametral tensile strength of the composite material was 44.5 $MN/m^2$.

EXAMPLE 17

1.0076 gm of 1,3=Bis[(p-acryloxymethyl) phenethyl]tetramethyldisiloxane was placed in a 25 ml glass vial. 7.5 mgm of photoinitiator camphorquinone and 4.5 mgm of activator ethyl-4,N,N-dimethyl aminobenzoate were successively added to the monomer. The mixture was then stirred until all the photoinitiator and the activator were dissolved. The addition and the mixing were performed in a dark room with the aid of a Kodak GBX-2 darkroom safelight to prevent the photo-induced polymerization. After thorough mixing, a mixture of inorganic filler was added to the monomer solution. The inorganic filler mixture consisted of 0.2540 gm of fumed $SiO_2$, Aerosil OX50 (Degussa Corp.) and 3.8249 gm of microcrystalline silica, IMSIL A-108 (Illinois Minerals) Both fillers had been treated with the organosilane coupling agent γ-methacryloxypropyl-trimethoxysilane before mixing. The monomer/filler composite mixture was thoroughly mixed until a homogeneous mixture was obtained. The hardness of the cured composite resin determined by Barcol Hardness instrument is 71. Water sorption of the cured polymer composite determined by the procedure described in the Example 4 is 0.19 $mgm/cm^2$, which is much lower than the currently known commercial dental composites. The diametral tensile strength of the composite determined according to the procedure described in Example 5 is 36.8 $MN/m^2$.

EXAMPLE 18

0.6367 gm of 1,3-Bis[(p-acryloxymethyl) phenethyl]tetramethyldisiloxane was placed in a 50 ml glass vial. 6.4 mgm of photoinitiator camphorquinone and 3.0 mgm of activator 2-dimethylamino ethyl methacrylate were successively added to the monomer. The mixture was stirred for an hour until the photoinitiator and the activator were all dissolved. The addition and the mixing were performed in a darkroom with the aid of a Kodak GBX-2 darkroom safelight to prevent the photo-induced polymerization. A inorganic filler mixture was first prepared and added to the monomer mixture. The filler mixture consisted of 0.2974 gm of fumed silica Aerosil OX50 (Degussa Corp.) and 4.4632 gm of Corning 7724 barium alumino borosilicate glass. Both fillers had been treated with the organosilane coupling agent γ-methacryloxypropyltrimethoxysilane before mixing. The monomer/filler composite mixture was thoroughly mixed until a homogeneous mixture was obtained. The hardness of the cured composite rein determined by Barcol Hardness instrument is 75. The diametral tensile strength of the composite is 40.2 $MN/m^2$. The cured polymer composite was milky white and translucent.

EXAMPLE 19

0.6103 gm of 1,3-Bis[(p-acryloxymethyl) phenethyl]tetramethyldisiloxane was placed in a 25 ml glass vial. 6.0 mgm of photoinitiator camphorquinone and 7.2 mgm of activator ethyl-4,N,N-dimethyl aminobenzoate were successively added to the monomer. The mixture was then stirred until all the photoinitiator and the activator were dissolved in the monomer. Next a filler mixture of amorphous silica fillers which consists of 0.2480 gm of Aerosil OX50 (Degussa Corp.) and 1.4914 gm of Silitex 22 (Kaopolite, Inc.) were prepared and thoroughly mixed. Both fillers had been treated with the organosilane coupling agent γ-methacryloxypropyl trimethoxysilane before use in the formulation. The monomer solution and the filler mixture were then thoroughly mixed until a homogeneous mixture was obtained. The photocured polymer composite is milky white and translucent, and exhibits nature tooth color. The hardness determined by Barcol Hardness instrument was 61. Water sorption of the cured polymer composite determined by the procedure described in the Example 4 was 0.10 $mgm/cm^2$, which is the lowest among known dental composites. The composite restorative material exhibited good color stability after immersion in water at 37° C. for a week.

EXAMPLE 20

0.3708 gm of 1,3-Bis[(p-acryloxymethyl) phenethyl]tetramethyldisiloxane was placed in a 25ml glass vial, into which 0.1923 gm of Bis-GMA, bisphenol A bis(2-hydroxylpropyl) methacrylate, was added. A 6.8 mgm of photoinitiator camphorquinone and 7.3 mgm of activator ethyl-4,N,N-dimethylaminobenzoate were successively added to the monomer mixture. The mixture was then stirred until all the photoinitiator and the activator were dissolved in the liquid monomer mixture. Next a filler mixture of amorphous silica fillers which consists of 0.4866 gm of Aerosil OX50 (Degussa Corp.) and 0.9831 of Silitex 22 (Kaopolite, Inc.) were prepared and thoroughly mixed. Both fillers are amorphous $SiO2$ and had been treated with the organosilane coupling agent γ-methacryloxypropyl trimethoxysilane before use in the formulation. The monomer solution and the filler mixture were then thoroughly mixed until a homogeneous mixture was obtained. The photocured polymer composite is milky white and translucent, and exhibit nature tooth color. The hardness determined by Barcol Hardness instrument was 70. Water sorption of the cured polymer composite determined by the procedure described in the Example 4 was 0.33 $mgm/cm^2$, which is lower than the currently known commercial dental composites. The composite restorative material exhibits good color stability after immersion in water at 37° C. for a week.

EXAMPLE 21

Dental composites similar to the one described in Example 18 were prepared, and used to determine the degree of conversion of the siloxane monomer 1,3-Bis[(p-acryloxymethyl) phenethyl]tetramethyldisiloxane in the dental composites induced by photopolymerization. The degree of conversion was studied by infrared multiple internal reflection spectroscopy-MIR, also called infrared attenuated total reflectance spectroscopy-ATR, using a Nicolet 5-DX FTIR spectrometer.

The composite film approximately 100um thick was coated on the surface of a KRS-5 crystal. The KRS-5 prism, 52×20×2 mm, 45° trapezoid crystal, was obtained from Spectra-Tec Inc. The coating of the siloxane composite films on the crystal and the curing of the films were performed in the dark under argon gas atmosphere within a glove bag to minimize the oxygen inhibition on photocuring. To obtain good contact between the composite film and the crystal, the film was covered by a microscopic slide and a hand vise was used to press the composite film to the KRS-5 crystal surface. Photocuring was conducted by placing the exit window of the curing light (Visilux 2, 3M Co.) on the glass slide and exposed the composite film for 1 minute through the glass plate. A total of 24 points across the entire film were exposed and each point was exposed for 1 minute.

MIR spectra of the siloxane composite films taken before and after the cure indicated that the intensity of the peak at 1636 cm$^{-1}$ decreased significantly while that of the peak at 1610 cm$^{-1}$ changed insignificantly. The decrease in the absorbance of the absorption band at 1636 cm$^{-1}$ which characterized the C=C stretching was due to polymerization. The absorbance of the peak at 1610 cm$^{-1}$ which characterized the C=C aromatic stretching was seen to remain intact. The degree of conversion was obtained by comparing the absorbance of the two peaks at 1636 and 1610 cm$^{-1}$ before and after cure.

The degree of conversion of the siloxane monomer 1,3-Bis[(p-acryloxymethyl) phenethyl] tetramethyldisiloxane in the composites was 90.0%. This is the highest percentage reported to date for any of the monomers used in present dental composites. This, of course, indicates a very high degree of cross-linking which, in turn, yields better mechanical properties including improved hardness and improved resistance to wear. The presence of fewer residual double bonds in the cured material also indicates that the material would be less likely to swell or to be degraded chemically in the oral environment.

It will be appreciated that the materials may be prepared from a single monomer species or a plurality of monomer species. The composite may be compounded with an amount of pre-polymerized and finely ground siloxane polymer in the form of a powder to further increase hardness and decrease cure time. The system may contain a variety of filler materials compatible with the system.

It will be appreciated from the above examples that visible light photocurable composite dental restoration materials have been prepared that exhibit superior desirable qualities. These include stable color, good hardness and tensile strength, reduced water sorption and the stability associated with a high degree of conversion of the monomer in the composite after cure.

This invention has been described herein in considerable detail in order to comply with Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A restorative dental composite material consisting substantially of:

an amount of at least one organosilicon monomer material selected from a class consisting of siloxane materials capable of being cross-linked and/or polymerized using light, the class of monomers being further characterized by compounds represented by a general structure selected from

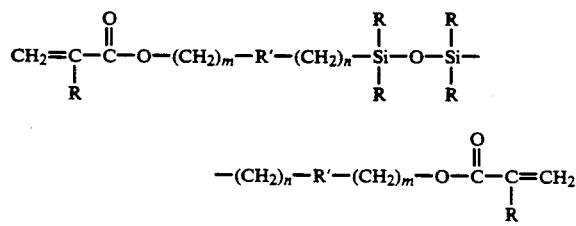

where

R is selected from a class consisting of a hydrogen atom, alkyl groups having from 1 to 5 carbon atoms, and aromatic groups consisting of phenyl and substituted phenyl groups, R' is selected from a class of aromatic groups consisting of phenyl and substituted phenyl groups, and m and n are integers equal to 1 or 2;

an amount of filler material;

an amount of coupling agent;

an amount of activator; and an amount of light sensitive photoinitiator.

2. The restorative dental composite of claim 1 further comprising an amount of a finely divided pre-polymerized siloxane polymer composite wherein the pre-polymerized siloxane polymer is prepared from one or more siloxane monomers selected from the class of claim 1.

3. The restorative dental composite of claim 2 wherein the pre-polymerized siloxane composite is of the same chemical composition as the restorative composite material.

4. The restorative dental composite of claim 2 wherein the pre-polymerized siloxane composite is thermally cured.

5. The restorative dental composite of claim 4 further comprising an amount of pigment material.

6. The restorative dental composite of claim 4 further comprising an amount of en ethylenically unsaturated monomer.

7. The restorative dental composite of claim 6 wherein the ethylenically unsaturated monomer is selected from the group consisting of dimethacrylates and diacrylates.

8. The restorative dental composite of claim 7 wherein the filler material contains an amount of ceramic material;

the coupling agent is selected from γ-methacryloxypropyl trimethoxysilane and vinyl triethoxysilane;

the activator is selected from ethyl-4,N,N-dimethylaminobenzoate, 2-dimethylamino ethyl methacrylate, and dimethylamino phenethanol; and the light sensitive photoinitiator is camphorquinone.

9. The restorative dental composite of claim 8 wherein the activator is 2-dimethylamino ethyl methacrylate.

10. The restorative dental composite of claim 7 wherein said ethylenically unsaturated monomer is bisphenol A Bis-2-Hydroxylpropyl) methacrylate.

11. The restorative dental composite of claim 8 further comprising an amount of pigment material.

12. The restorative dental composite of claim 8 wherein the pre-polymerized siloxane composite is of the same composition as the restorative dental composite material.

13. The restorative dental composite of claim 1 further comprising an amount of pigment material.

14. The restorative dental composite of claim 1 including an amount of an ethylenically unsaturated monomer.

15. The restorative dental composite of claim 14 wherein the ethylenically unsaturated monomer is selected from the group consisting of dimethyacrylates and diacrylates.

16. The restorative dental composite of claim 15 wherein:

the filler material contains an amount of ceramic material;

the coupling agent is selected from γ-methacryloxypropyl trimethoxysilane and vinyl triethoxysilane;

the activator is selected from ethyl-4,N,N-dimethylaminobenzoate, 2-dimethylamino ethyl methacrylate, and dimethylamino phenethanol; and the light sensitive photoinitiator is camphorquinone.

17. The restorative dental composite of claim 16 wherein the activator is 2-dimethylamino ethyl methacrylate.

18. The restorative dental composite of claim 16 further comprising an amount of pigment material.

19. The restorative dental composite of claim 15 wherein said ethylenically unsaturated monomer is bisphenol A Bis-2-Hydroxylpropyl) methacrylate.

20. The restorative dental composite of claim 1 wherein the filler material contains an amount of ceramic material.

21. The restorative dental composite of claim 1 wherein the photoinitiator is sensitive to visible light.

22. The restorative dental composite of claim 1 wherein the photoinitiator is sensitive to UV light.

23. The restorative dental composite of claim 1 wherein:

the filler material contains an amount of ceramic material;

the coupling agent is selected from γ-methacryloxypropyl trimethoxysilane and vinyl triethoxysilane;

the activator is selected from ethyl-4,N,N-dimethylaminobenzoate, 2-dimethylamino ethyl methacrylate, and dimethylamino phenethanol; and the light sensitive photoinitiator is camphorquinone.

24. A restorative dental composite material consisting substantially of:

an amount of an organosilicon monomer having the structural formula

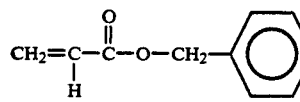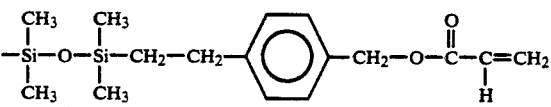

an amount of ceramic-containing filler material;

an amount of a coupling agent selected from γ-methacryloxypropyl trimethyoxysilane and vinyl triethoxysilane;

an amount of camphorquinone photoinitiator; and an activator comprising an amount of material selected from 2-dimethylamino ethyl methacrylate and ethyl-4,N,N-dimethyl aminobenzoate.

25. The restorative dental composite material of claim 24 further comprising an amount of bisphenol A Bis-2-Hydroxylpropyl) methacrylate monomer.

26. The restorative dental composite material of claim 25 further comprising an amount of thermally pre-polymerized particles of the same composition as the siloxane restorative dental composite material.

27. The restorative dental composite material of claim 26 wherein the ceramic filler contains an amount of material selected from borosilicate glass, fumed silica, fused silica and crystalline silica.

28. The restorative dental composite material of claim 25 further comprising an amount of pigment.

29. The restorative dental composite material of claim 24 further comprising an amount of finely divided thermally pre-polymerized particles of the same composition as the restorative dental composite material.

30. The restorative dental composite material of claim 24 further comprising an amount of pigment.

31. The restorative dental composite material of claim 24 wherein the ceramic filler contains an amount of material selected from borosilicate glass, fumed silica, fused silica and crystalline silica.

* * * * *